United States Patent [19]
Schouten

[11] Patent Number: 5,919,209
[45] Date of Patent: Jul. 6, 1999

[54] SYSTEM AND METHOD FOR MYOCARDIAL REVALIDATION AND THERAPY BY HIGH RATE PACING

[75] Inventor: Vincent J. A. Schouten, Cadier en Keer, Netherlands

[73] Assignee: Medtronic, Inc., Minneapolis, Minn.

[21] Appl. No.: 08/645,471

[22] Filed: May 13, 1996

[51] Int. Cl.[6] .................................................. A61N 1/362
[52] U.S. Cl. .................................................................. 607/2
[58] Field of Search ................................... 607/9, 14, 15, 607/2

[56] References Cited

U.S. PATENT DOCUMENTS

| | | |
|---|---|---|
| 4,541,417 | 9/1985 | Krikorian . |
| 4,787,389 | 11/1988 | Tarjan . |
| 4,884,575 | 12/1989 | Sanders . |
| 4,922,930 | 5/1990 | Adkins et al. . |
| 5,213,098 | 5/1993 | Bennett et al. . |
| 5,423,869 | 6/1995 | Poore et al. ............................... 607/18 |
| 5,514,162 | 5/1996 | Bornzin et al. ........................... 607/19 |

FOREIGN PATENT DOCUMENTS

| | | | |
|---|---|---|---|
| 0 541 338 A1 | 11/1992 | European Pat. Off. | A61N 1/365 |
| WO 86/07270 | 12/1986 | WIPO | A61N 1/36 |
| WO 87/00760 | 2/1987 | WIPO | A61N 1/36 |

OTHER PUBLICATIONS

"Effect of exercise conditioning on excitation–contraction coupling in aged rats" by Judith K. Gwathmey et al;The American Physiological Society 1990.

"Diastolic Dysfunction and Congestive Hart Failure" by William Grossman, MD, Pathophysuiology, Supp. III, vol. 81, No. 2, Feb. 1990.

"Neuroendocrine Manifestations of Congestive Heart Failure" by Gary S. Francis MD, The American Journal of Cardiology, Jul. 11, 1988.

"Effects of physical training in chronic heart failure" by Andrew J.S. Coats et al, The Lancet, vol. 335.

"Congestive heart failure: A review of nonpharmacologic therapies" by Gisele LoRusso Bousquet MS,RN, Cardiovasc Nurs 1990;4(3);35–46, 1990.

(List continued on next page.)

*Primary Examiner*—Scott Getzow
*Attorney, Agent, or Firm*—Michael J. Jaro; Harold Patton

[57] ABSTRACT

There is provided a system and method for high rate pacing of patients for training, or revalidation of heart muscle. The system and method of this invention provide a therapy particularly directed for patients with CHF, to enable effective exercise of the cardiac muscle without requiring the patient to exercise. In another embodiment, an alternate high rate routine, or algorithm is provided for assisting a patient to exercise during at least some part of the high rate pacing routine. The high rate pacing therapy may be initiated either automatically, based upon the patient's circadian rhythm; automatically by patient data sensed by a system of sensors; or may be initiated directly by the patient by use of a simple external programmer device. The pacemaker of the invention suitably stores a plurality of algorithms which can be selected, or which can be modified or replaced by an external programmer. Whether used by a CHF patient or a patient who does not have CHF but who is in danger of developing it, the exercise algorithms suitably provide for high rate pacing in the range of about 90–160 bpm. For a CHF patient, the high rate pacing is carried out for a duration in the area of about 20 minutes, preferably twice a day. The duration and frequency of therapy can be programmed to match patient needs, and may vary from only several minutes to much greater than 20 minutes, carried out 1, 2 or more times daily, or automatically based upon patient data.

34 Claims, 4 Drawing Sheets

OTHER PUBLICATIONS

"Reduced Subendocardial Coronary Reserve: A Potential Mechanism for Impaired Diastolic Function in the Hypertrophied and Failing Heart" by Stephen F. Vatner, MD et al, Department of Medicine, Harvard Med. School.., Supp.III, vol.81, No.2, Feb.1990.

"Skeletal Muscle Metabolic Dysfunction: Implications for Exercise Intolerance in Heart Failure" by John R. Wilson, MD et al, Card. Vas. Section, Dpt. Medicine, U. of Penn, Supp. VII vol. 87,No.6, Jun. 1993.

Controlled Trial of Physical Training in Chronic Heart Failure—Exercise Performance, Hemodynamics, Ventilation, and Autonomic Function—Andrew J.S. Coats et al. (Circulation, vol. 85, No. 6, Jun. 1992, pp. 2119–2131).

SYSTEM AND METHOD FOR MYOCARDIAL REVALIDATION AND THERAPY BY HIGH RATE PACING

BACKGROUND OF THE INVENTION

This invention relates to a cardiac pacing system and method for treating patients with congestive heart failure, or patients who are likely to develop congestive heart failure, and in particular as a system and method for periodic high rate cardiac pacing of such patients.

Congestive heart failure (CHF) is an extremely serious affliction. CHF has a great impact on the quality of life; it involves the loss of heart rate variability and rate responsive mechanisms in the heart, leading to impaired ventricular relaxation and low exercise tolerance. The disease afflicts about 4 million Americans in any given year; in the USA alone, there are annually about 400,000 new cases, 1 million hospital admissions, and $8 billion cost of care. While drug treatment improves quality of life, it has little effect on survival. Current pharmacologic treatment includes a combination of diuretics, vasodilators, inotropes, β-blockers, and Angiotensin-Converting-Enzyme (ACE)-inhibitors (Bristow & Gilbert, 1995, "Improvement in Cardiac Myocyte Function by Biological Effects of Medical Therapy: A New Concept in the Treatment of Heart Failure," *European Heart Journal* 16, Supplement F: 20–31). The effect is a decrease of symptoms, and improved quality of life, but little change in mortality. Moreover, the exercise tolerance of most patients is extremely low, as a consequence of limited oxygen supply through the lungs. Long lasting lack of exercise and malnutrition may contribute to the condition and partly explain the exercise intolerance. Indeed, the lack of exercise and deterioration of cardiac muscle may each contribute to each other, with a snowballing effect (Coats et al., 1992, "Controlled Trial of Physical Training in Chronic Heart Failure: Exercise Performance, Hemodynamics, Ventilation, and Autonomic Function," *Circulation* 85: 2119–2131).

Heart failure develops generally in the course of months or years, and can be the end stage of chronic hypertension, infarction, angina, or diabetes. Heart failure, however caused, represents an intrinsic property of the muscle, and slow relaxation due to slow intracellular calcium removal by the sarcoplasmic reticulum is an important factor. In the normal, healthy heart the duration of contraction and relaxation decreases with increasing heart rate. This ensures a diastolic period of sufficient duration, which is important (a) for filling of the ventricle, and (b) because coronary perfusion and myocardial oxygen supply occurs only during diastole. The duration of contraction and relaxation is determined by calcium removal from the contractile filaments, mainly by the calcium pump in the sarcoplasmic reticulum. Increased heart rate causes more rapid relaxation due to increased activation of the calcium pump. The latter mechanism is impaired in the hypertrophied or failing heart due to reduced transcription of the genes that supply the calcium pump proteins. Therefore, in heart failure patients an increase of heart rate may almost abolish the diastolic interval, which leads to reduced ventricular filling, and reduces myocardial blood supply (Davies et al., 1995, "Reduced Contraction and Altered Frequency Response of Isolated Ventricular Myocytes From Patients With Heart Failure," *Circulation* 92: 2540–2549).

In view of the above, the system and method of this invention provide a therapy designed to exercise the heart of a CHF patient in a manner that can be easily tolerated by the patient, and without complications. The basic feature of the therapy provided by the invention is to pace the patient's heart for relatively short periods of the day and at a high rate, eg., 140 beats per minute (bpm) for 20 minutes, once or twice daily. The effect of this pacing regimen is to mimic the effect on the heart of patient training, or exercise. The purpose of the therapy is to provide large variations in heart rate which are designed to enhance the heart's rate responsive mechanisms, eg, rate-dependent activation of the calcium pump. For the patient with CHF, this can be done without the complications which may be associated with normal physical exercise.

The therapy provided by the system and method of this invention is applicable either to patients who already have CHF, or to patients who are indicated as likely near term candidates for developing CHF. For patients with CHF, the system provides therapy which exercises the heart without the complications associated with normal physical exercise. For patients who do not have CHF but who are in danger of CHF, the system provides for automatically scheduled or patient-enabled high rate pacing of a form and duration adapted to a patient's tolerance of exercise, so that the patient can establish an exercise regimen which will improve heart function, peripheral circulation, skeletal muscle properties and neurohormonal function.

The premise of the therapy provided by this invention is that the rate responsive mechanisms in the heart muscle are enhanced by pacing with episodes of high rates. It is known that in general physiologic mechanisms tend to adapt to changing demands and that, in particular, muscle fibers can be transformed by proper stimulation protocols. In normal subjects, heart rate varies continuously throughout the day, related to the circadian rhythm, breathing, and blood pressure regulation; transients of high rate occur particularly during physical exercise. The variations in heart rate, however, are relatively small in patients with myocardial infarction, coronary artery disease, and in patients with hypertrophy or heart failure. On the other hand, the literature discloses that ventricular relaxation in old rats is much slower than in young rats; but that exercise training led to faster relaxation in the old rats (Gwathmey et al, 1990, *J. Appl Phsiol* 69: 1366–1371). The enhanced relaxation may be a long-term adaptation to the transient heart rate increases during exercise. Insulin is an important hormone in the regulation of normal cell growth and differentiation. There are indications that in animals with myocardial hypertrophy insulin may prevent or delay the transition to heart failure. (Rupp et al, 1988, *Biochem Biophys Res Comm* 156:917–923). It has been suggested that exercise may increase the insulin sensitivity in the heart. (Roubenoff and Rall, 1993). Therefore, periodic high rate pacing may increase the insulin sensitivity in the heart.

It is to be noted that there are potential adverse effects to high rate pacing, which the system and method of this invention must take into account. In the chronic ischemic heart, high rate pacing may lead to increased diastolic pressure, indicating calcium overload and damage of the muscle fibers. For this reason, the disclosed therapy may not be applicable to such patients. For a patient with CHF where the therapy is applied without exercise and concomitant activation of skeletal muscles, the result is an increase in oxygen consumption in the heart only, i.e., general hypoxia in the body will not occur. In failing hearts with relatively normal coronary arteries end-diastolic volume and pressure decrease with increasing heart rate; this may improve cardiac blood supply. However, in patients with advanced CHF, the endocardial coronary reserve is often exhausted.

Therefore, the therapy provided by this invention may not apply to patients with end-stage failure, and in any event the maximum pacing rate applied must be adjusted for each patient so as to maintain it below the rate at which myocardial hypoxia develops.

SUMMARY OF THE INVENTION

It is an object of this invention to provide a high rate pacing system and method for treating patients with CHF, or patients having a condition likely to lead to CHF. Accordingly, there is provided a system and method for high rate pacing, wherein a patient is paced with high rate episodes either periodically, or upon patient demand. For the CHF patient, there is provided a control algorithm calculated, or designed to provide high rate pacing therapy which will train, or revalidate the cardiac muscle without requiring exercise on the part of the patient. In another embodiment, for patients who do not yet have CHF, the pacing system employs an algorithm designed to provide a pacing therapy which both trains the heart and provides an environment which enables the patient to exercise, so that the patient gets the benefit of both cardiac training and training of skeletal muscle.

In a preferred embodiment, the pacing and method of this invention provide for pacing of the patient at a high rate in a range of about 90–160 bpm, and preferably at least about 130 bpm, and for a duration of up to 30 minutes, and preferably 20 minutes. The algorithm for controlling the high rate episode may suitably include a start-up duration wherein the pacing rate is ramped or otherwise increased to the desired high rate, as well as a post-high rate duration wherein the pacing rate is dropped back to a normal rate. The system includes one or more sensors to monitor heart responsiveness to rate variations, and in particular the high rate pacing, the sensor signals being utilized to either adjust the high rate pacing algorithm or terminate the algorithm in the event that it is indicated that the heart is not responding well to the high rate episode.

DESCRIPTION OF THE PREFERRED EMBODIMENTS

Figure 1:
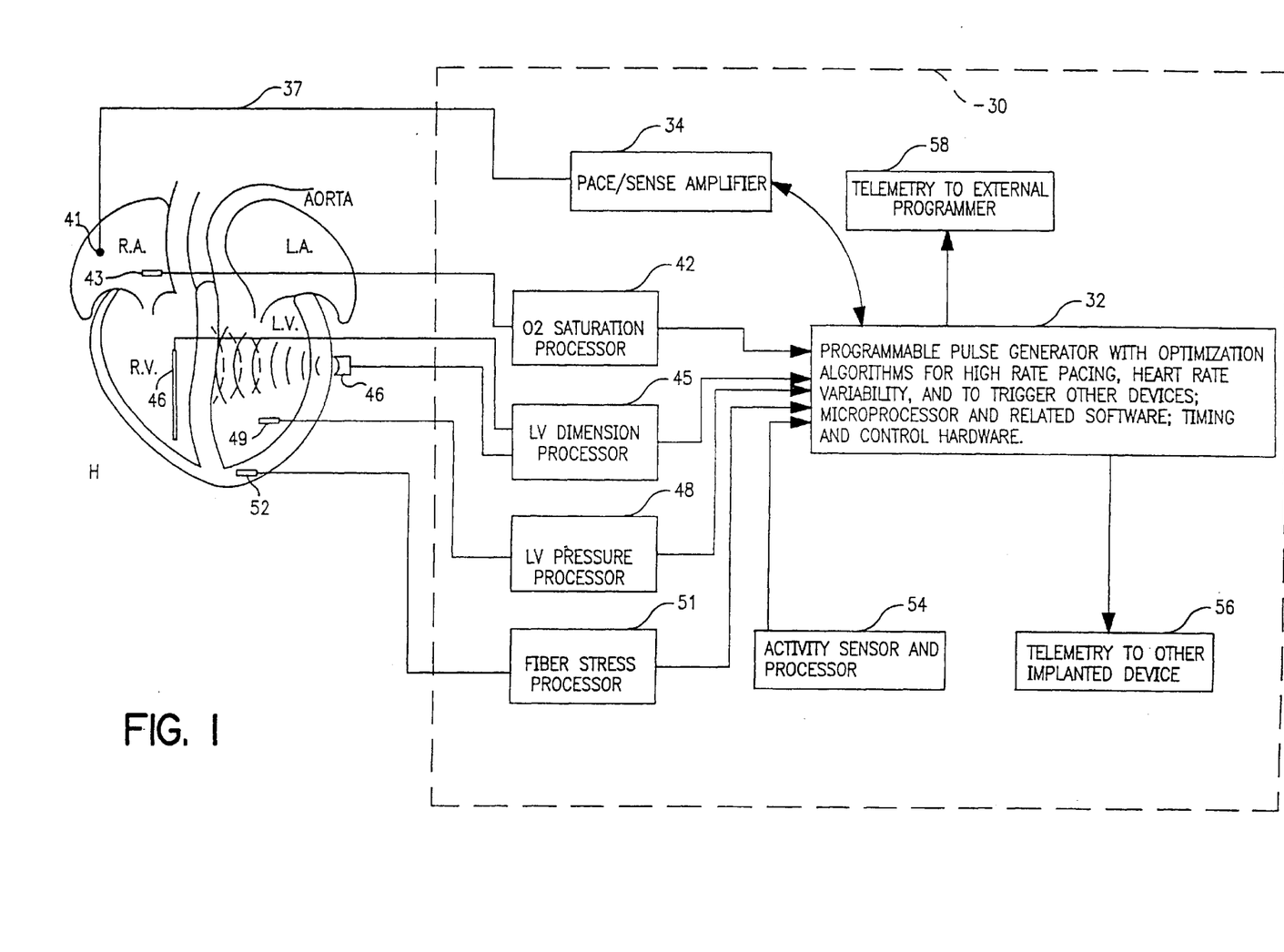
FIG. 1 is a diagrammatic representation of a pacemaker system in accordance with this invention, showing periodic high rate pacing with sensor control of such high rate pacing.

Referring now to FIG. 1, there is shown a diagram of a pacemaker 30 in conjunction with a patient's heart H. FIG. 1 is illustrative of the basic features of a pacing system which enables high rate pacing for providing therapy to patients with CHF or prospective CHF, as discussed above. It is to be noted that this figure is not an attempt to set forth all of the required features with all of the components of a modern pacemaker, such as are known to those of skill in the art. As an illustration of a modern pacemaker, see U.S. Pat. No. 5,342,406, incorporated herein by reference.

Block 32 represents a programmable pulse generator with control including one or more optimization algorithms for high rate pacing, heart rate variability as well as for developing trigger signals to trigger other devices. Thus, block 32 embraces a pace pulse generator, and associated control and logic circuitry, preferably including a microprocessor and associated memory. The pacemaker is in communication with an external programmer through transmit/receive block 58, whereby it can transmit data to the external programmer and receive program data. The pulse generator thus can be programmed to operate with a selected algorithm for optimizing a high rate pacing episode. Further, it can be programmed to adjust a prior stored algorithm, based on physician input. In general, a high rate episode is driven by an algorithm to provide pacing at at least a predetermined high rate H for a duration D, the algorithm to be used one or more times $T_x$ of the day. The algorithm controls a high rate pacing episode, which may have a rate vs. time characteristic as desired. As an example of an ultimately simple algorithm, the pacing rate would simply be raised from some normal level (e.g., 70 bpm or the spontaneous rhythm of the heart) to a predetermined high rate (e.g., 130 or 140 bpm) for a duration D and then dropped back down. Of course, the pacemaker may be rate responsive, such that the rate at the start and end of the episode would be variable and determined by sensed metabolic need. Further, the algorithm preferably provides for a gradual transition from lower rate to the high rate which is to be sustained for a desired duration of time, e.g., 20 minutes. Thus, the envelope with the rate variation may be rectangular, triangular or any other shape, and additionally may be adjusted or modulated on a basis of sensor inputs, as discussed in more detailed below.

Algorithms useful for the pacemaker system of this invention include the following:

algorithms that control pacing stimulus rate in response to one or more sensor inputs, e.g., switch off high rate pacing or reduce the rate of the episode;

algorithms that continually calculate an index ($IN_x$ of myocardial responsiveness to rate change) based on sensor inputs, and adjust the stimulus rate and/or store data concerning heart performance for later diagnostic evaluation;

algorithms that monitor inputs relating to cardiac performance and responsiveness, and control activity of another implanted or external device, e.g., drug pump for injection of β-blocker (or another cardiovascular drug) a given time interval before initiating high rate pacing, or a pulse generator for stimulation of nerves or receptors before, during and/or after high rate pacing.

Thus, the algorithms control the profile or characteristics of the high rate pacing episode; the collection of data relevant to the high rate pacing therapy, both during high rate episodes and between such episodes; and general cardiac pacing and other therapies administered in conjunction with the high rate pacing.

Still referring to FIG. 1, pace pulses are delivered through a lead 37 to the patient's heart, illustrated as being delivered by an electrode 41 in the right atrium. It is to be understood that the invention is applicable to single chamber or dual chamber pacing, unipolar or bipolar, and is not limited to the chosen mode of pacing. As in a conventional pacing system, the signal is picked on the heart, returned through the lead (or leads 37), processed in sense amplifier 34, and utilized by the pacemaker logic.

FIG. 1 shows a plurality of sensors, which are illustrative of the type of sensor feedback utilized in this invention. As discussed above, high rate pacing under certain patient circumstances may be dangerous or otherwise not indicated, and accordingly a sensor feedback system with a very short response time is important in the practice of this invention. There is illustrated an oxygen saturation sensor 43, connected to an O2 saturation processor 42, the output of which is coupled to block 32. Venous O2 saturation is an important parameter for judging the efficacy of the high rate pacing. LV dimension elements 46, 46' provide signals which are inputted to LV dimension processor 45, providing a measure of ventricular volume, and depiction of acute decompensation and/or muscle stress. LV pressure transducer 49 has an output connected to LV pressure processor 48, for detecting ventricular pressure and/or rate of pressure dP/dt. Instead of the left ventricle, the sensors may also be used to measure pressure and volume in the right ventricle (RV). Fiber stress sensor 52 is connected to fiber stress processor 51, for providing an indication of cardiac muscle stress during the high rate episode, or routine. All of this sensor data can be used together, or selectively for controlling the high rate algorithms. In addition, an activity sensor and processor 54 are located within the pacemaker can, and provide further useful information for adjusting or controlling the high rate algorithms, as is discussed in more detail below. FIG. 1 also illustrates a telemetry output to one or more other implanted devices, which may be used as part of the system of this invention, as discussed above.

With this background, the different applications of the system of this invention and the corresponding therapies for the patient, can be discussed in more detail. The primary application is directed to the CHF patient, and involves increasing pacing rate periodically, e.g., within a range of 90–160 bpm for a duration of preferably 10–20 minutes, and preferably twice a day. The high rate can vary within this range, but in order to provide maximum benefit it is desired to carry out the high rate episode for at least 20 minutes. The exact rate, and indeed the variation of rate during any given episode, is something that can be programmed by the physician who has knowledge of the patient, and adjusted either automatically or by subsequent programming in view of feedback concerning cardiac and patient responsiveness to the high rate episodes. The important point is that the high rate algorithm is predetermined, or calculated to provide a high rate episode for exercising the patient's heart, without need for the patient to exercise.

In a first preferred embodiment, the cardiac high rate episodes are based on the patient's circadian cycle. For example, two episodes of increased rate can be programmed daily, scheduling the episodes for when the patient is presumed to be awake. Alternately, the high rate episodes can be patient-controlled, by use of a simple device which can constitute simply a magnet, or a more sophisticated type of programmer. For a CHF patient having an implanted pacemaker programmed to provide one or two episodes per day, the patient is suitably enabled only to deactivate the programmed high rate episodes. A patient who is able to exercise, and who desires to combine physical exercise with a high rate routine, may be enabled to activate a routine specifically adapted for accompanying patient exercise. Such an exercise-related routine is specifically calculated to provide a high rate variation adapted to the patient's ability to exercise. For example, if the patient can only exercise for a short period, e.g., 3–10 minutes, the routine can control a high rate calculated to assist exercise for such a first duration, and then optimally provide a second duration, e.g., another 10–15 minutes, calculated as a non-exercise high rate routine. Further, a patient can utilize a modified routine which includes a "pre-exercise" time period wherein the heart rate is increased before the patient starts to exercise, as well a post-exercise period of rate decrease. Such a pre-exercise portion of the episode is controlled by a stored algorithm, and may be accompanied by controlling an implanted drug pump for injection of a β-blocker or another drug a given time interval before or after the onset of high rate pacing. Thus, the system may embrace both a specially adapted pre-exercise pacing routine and additional therapy administered before the anticipated exercise, to condition and aid the patient to tolerate the exercise to be undertaken.

Another feature of the system of this invention is to provide the patient with real time information during a high pacing episode, and particularly when the patient is undertaking exercise in addition to the pacing therapy. For this reason, the system includes a simple output device used by the patient, to which the implanted pacemaker can transmit data concerning pacing rate, activity rate and any other sensed cardiac parameter, to be displayed on a readout screen mounted on the patient's external device. This data can include advising a user when his or her condition is suitable for undertaking exercise. The invention also includes transmitting summary data after the conclusion of an episode, with or without exercise, giving the patient a profile of cardiac response in terms of heart rate and/or exercise workload.

In another embodiment of the invention, an activity sensor is used to maintain a history of patient exercise. If the patient exercise data shows that the daily exercise level has dropped below a minimal threshold, this information is used by a stored algorithm to trigger a high rate routine which reflects the relative amount of exercise that the patient needs. In addition, the system embraces improved diagnostics in the form of data stored for optimizing the high rate routine and for providing a physician with information concerning the patient's cardiac history. For the patient with CHF who does not exercise, the algorithm, or high rate routine, is suitably adjusted based upon sensed cardiac reaction to the high rate pacing. For a patient who exercises at least some time during the high rate routines, or episodes, there is provided a comparison of the activity count vs. rate over the time of the routine as well as tracking of the sensor data which indicates the degree of cardiac responsiveness. The outputted data informs the patient when it is safe to commence exercise, and whether exercise should be halted.

Figure 2:
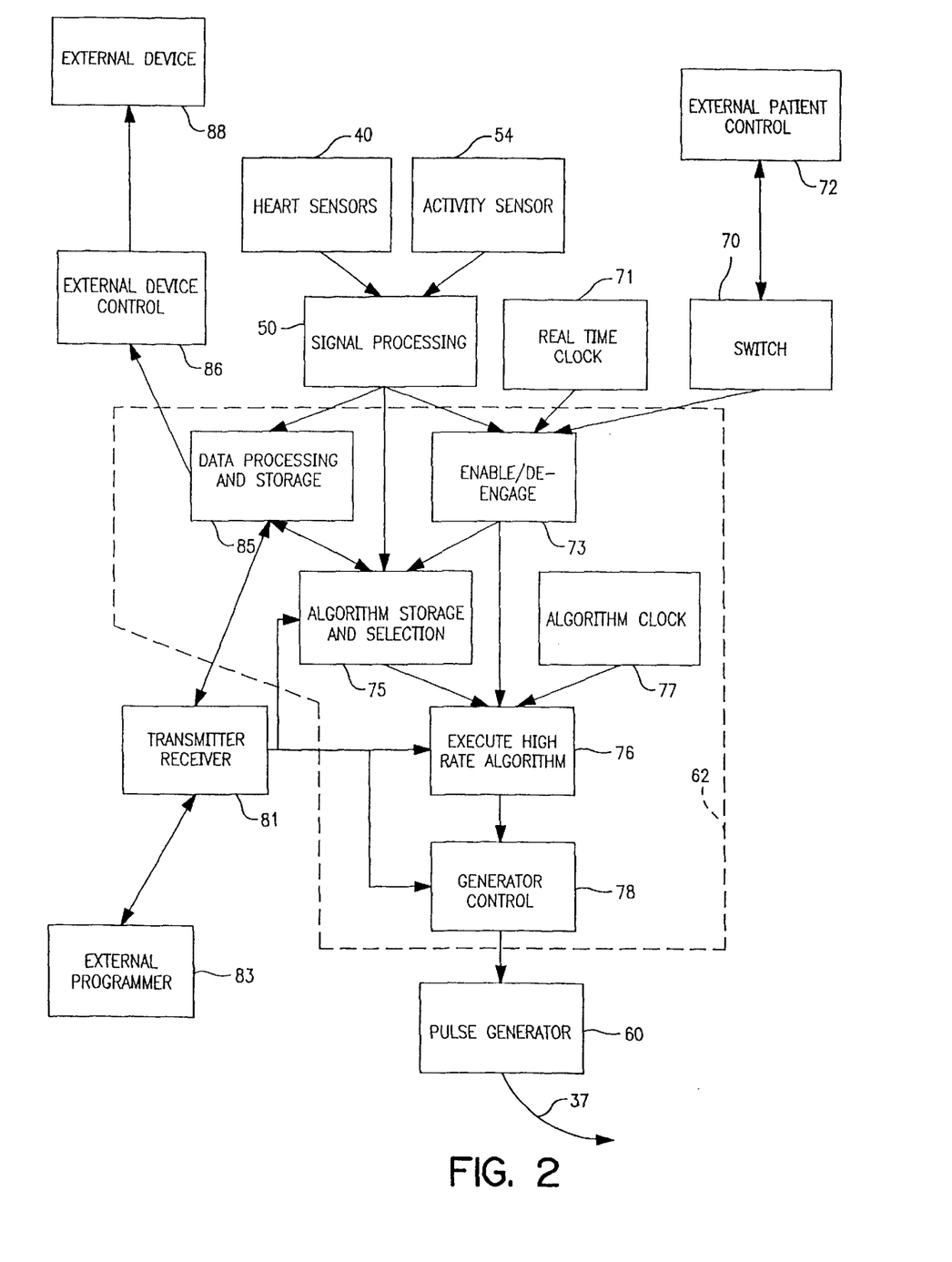
FIG. 2 is a block diagram of a pacemaker system in accordance with this invention, showing in more detail the functional components for providing high rate pacing therapy.

Referring now to FIG. 2, there is shown within dashed lines a control portion 62 of a pacemaker in accord with this invention. The functions indicated within control portion 62 are preferably carried out by a microprocessor or equivalent logic device, in association with software which is stored and can be adjusted by an external programmer, or automatically on the basis of sensed information. As seen, there are a number of inputs to control portion 62, these inputs including sensor inputs, externally generated inputs and a clock input. Heart sensors 40, as discussed above, provide signals which are inputted to sensor processors 50, which amplify and otherwise process the sensor signals into a digital form suitable for use. Activity sensor 54 is shown as a separate sensor, providing signals representative of patient activity. The signals from block 50 are inputted to the algorithm storage and selection block 75, where they may be used to control selection of one of a plurality of algorithms stored within the pacemaker. Outputs from block 50 are also connected to enable/de-energize block 73, which provides outputs to blocks 75 and 76, for either enabling or terminating the operation of a high rate algorithm which has been selected at block 75. Switch 70, illustrated as suitably a simple closed/open reed switch, also provides an output to enable/de-energize block 73. The reed switch is shown as being activated by an external patient control 72. Also illustrated is a real time clock 71, which may be used to enable or de-energize a selected algorithm for carrying out a high rate episode, e.g., in accordance with the patients circadian rhythm.

The high rate algorithm selected at 75 is transferred to block 76, where it is operated in conjunction with an algorithm clock illustrated at 77. The high rate algorithm logic signals are coupled to generator control 78, which in turn controls the pulse generator 60. The transmitter/receiver 81 within the pacemaker is shown in communication with an external programmer 83. The external programmer may be a sophisticated programmer for forwarding programming signals, and receiving data from the pacemaker. The transmitter/receiver may also communicate with a simple patient device as shown at 72 to provide useful information during an episode, e.g., whether exercise is permitted.

Still referring to FIG. 2, an output from sensor processor block 50 is shown being connected to data processing and memory block 85. At 85, the sensor data is suitably processed, e.g., such as by accumulating activity signals, and stored. This processed data may be used to couple a control signal to algorithm and selection block 75. The data processing and memory block 85 is in communication with external device control block 86, which in turn is adapted to transmit signals to an external device as illustrated at 88. As discussed above, external device 88 may suitably be an implanted pump, or other device for operation in conjunction with the pacing therapy of this invention. The control block 86 may be external, may be an internal device, or may be located in the pacemaker.

Figure 3:
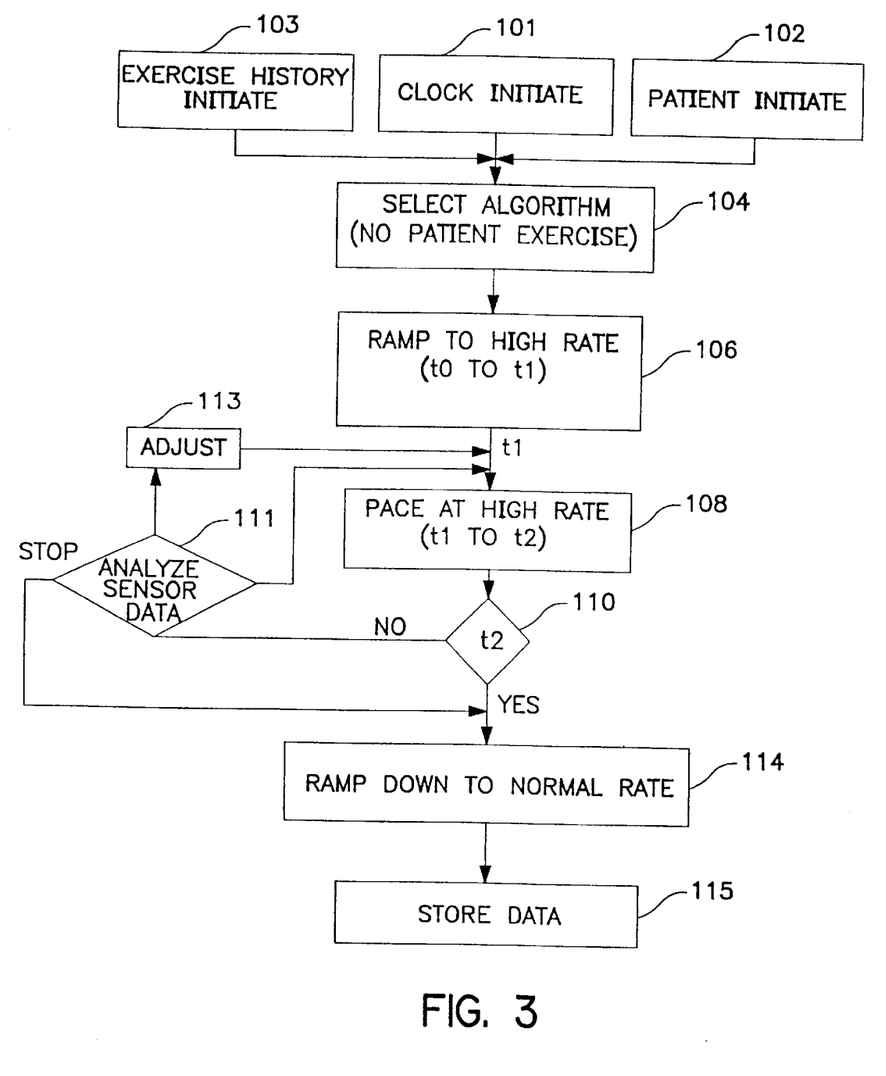
FIG. 3 is a flow diagram of steps taken in applying the therapy of this invention to a patient with CHF, wherein the patient undertakes no exercise during the high rate episode.

Referring now to FIG. 3, there is shown a flow diagram of steps taken for carrying out a pacing therapy for a patient who has CHF, and receives high rate pacing therapy without doing any exercise during the therapy. Therapy may be initiated by a simple clock interrupt, as shown at 101, which provides initiation of therapy in accordance with the patient's circadian rhythm. Alternately, as shown at 102, the patient may initiate the therapy by transmitting a signal to the implanted pacemaker. In another arrangement, there may be an initiation based on exercise history, as shown at block 103. From whatever source the initiate signal comes, an algorithm is selected at block 104. The algorithm initiates the therapy episode by ramping to a high rate, doing this from time $t_0$ to $t_1$, as shown at block 106. Then, as shown at 108, the patient is paced at the high rate from $t_1$ to time $t_2$. Assuming that the time $t_2$ has not been reached, the algorithm has a loop through block 111, to continually analyze sensor data. The sensor data analysis step may result in maintaining pacing in accordance with the algorithm, by returning to block 108. Alternately, it can cause an adjustment of the algorithm, e.g., lowering the rate, in which an adjustment is made at 113. Following the adjustment at 113, the routine can return to 108, as shown, or go to another block (not shown) to adjust rate gradually. Also, the algorithm can be terminated by jumping to block 114. If the algorithm is not terminated, it carries on until time $t_2$ has been reached, whereupon it exits to block 114 where the pacer rate is ramped down to the normal rate. Following this, data relating to the episode is stored at 115.

Figure 4:
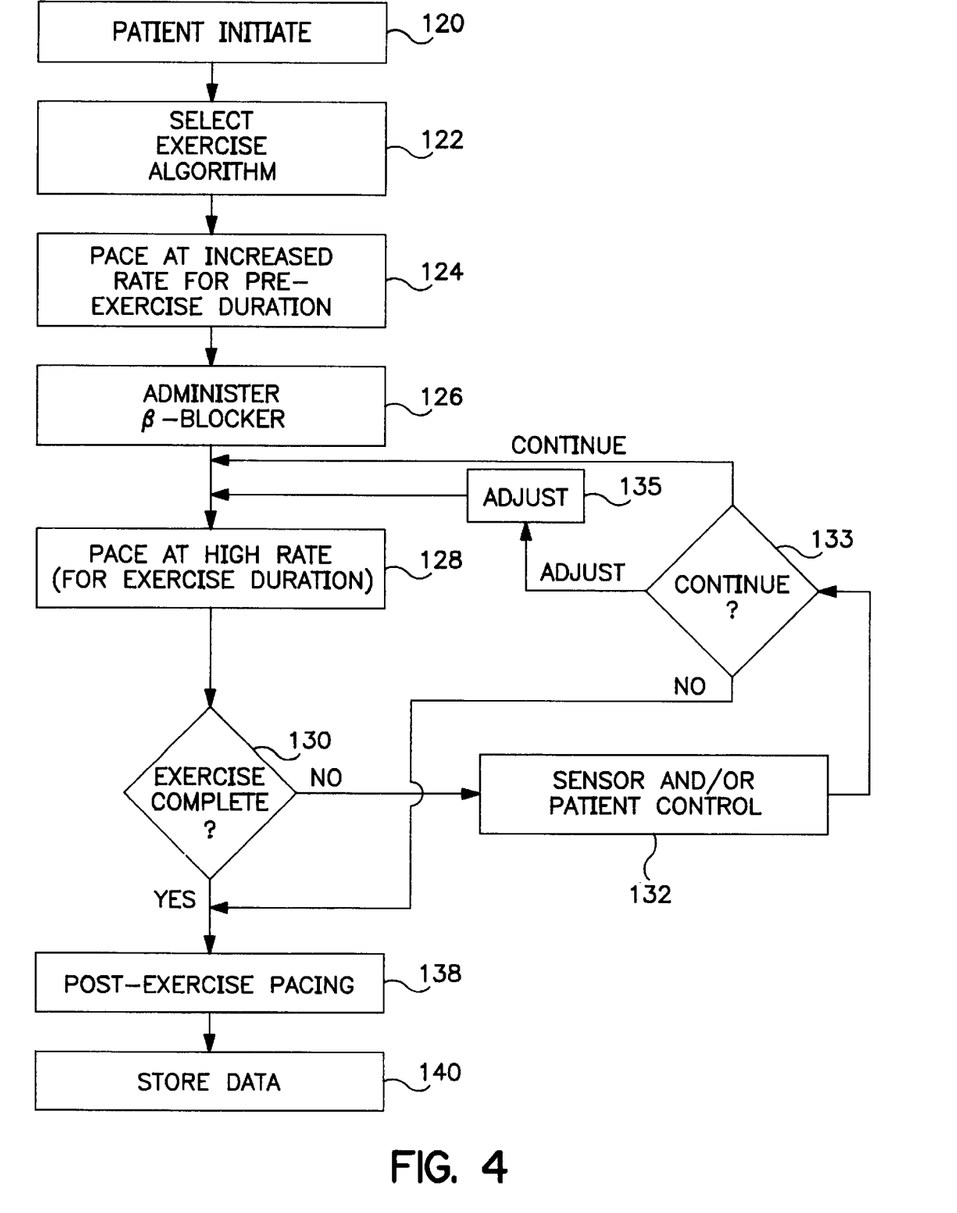
FIG. 4 is a flow diagram of steps taken in applying the therapy of this invention to a patient with early stage CHF, or who has not yet developed CHF, wherein the patient may undertake exercise during the high rate episode.

Referring now to FIG. 4, there are shown the steps of a routine modified to aid a patient in exercising. The patient initiates this routine as indicated at 120, whereupon a suitable exercise algorithm is selected at 122. At 124, the algorithm paces the patient at an increased rate for a pre-exercise duration, e.g., several minutes. The increased rate may be a ramp-up of rate, or simply a step increase in rate to an intermediate rate above the patient's prior rate. Note that for such a patient who is able to undertake exercise, or even a patient with CHF, the pacemaker may not normally be pacing the patient, i.e., the pacemaker may be quiescent except for the high rate pacing episodes.

Continuing to block 126, the routine may optionally administer a β-blocker or another drug, or take any other step concurrent with preparing for exercise. Then, at 128, the routine causes pacing at a high rate, for a duration calculated in accordance with the expected time that the patient will exercise. The routine enters a loop and at 130 determines whether the exercise duration is complete. If not, the routine continually checks sensor and/or patient control, as indicated at block 32. At block 133 a decision is made as to whether to continue the routine, adjust it, or simply exit. If the routine is to be adjusted, this is done at block 135. If the routine is to be exited, which is also the case when exercise duration is found to be complete at block 130, the routine goes to the post-exercise pacing portion, shown at block 138. This is suitably a ramp-down of pacing rate, suitably to a normal pacing rate. Following this, data concerning the high rate pacing episode is stored at 140. This data may suitably be data providing a comparison of cardiac responsiveness to activity level during the pacing episode, for use in adjusting the high rate pacing algorithm for subsequent episodes.

The invention is seen to embrace a wide scope of pacing therapy routines. For the CHF subject who cannot exercise, the routine preferably extends for 20 minutes, and is undertaken at least twice daily. For a pre-CHF subject, the routine is more likely to be adopted to helping build up a capacity for exercise. Thus, the system and method of invention include any arrangement of therapy routines, or episodes, including shorter duration episodes of only several minutes undertaken more frequently. The duration is determined for any particular subject based upon an analysis of the cardiac condition and tolerance of exercise, and how much high rate pacing will provide beneficial cardiac exercise. The determined duration can be adjusted by external programming, by the subject, or automatically as a function of system sensor feedback.

I claim:

1. A cardiac pacing system having a pacemaker with a pace pulse generator, and at least one lead for delivering pace pulses from said pacemaker to a patient's heart, said pacemaker having rate control means for controlling the rate of pace pulses generated by said pace pulse generator, said rate control means comprising:

high rate means for controlling said generator to continuously generate said pace pulses at a high rate in a range of about 90–160 bpm and for a high rate episode of a predetermined duration, said high rate means further comprising algorithm means for controlling the rate variation and duration of a said high rate episode.

2. The system as described in claim 1, wherein said algorithm means has duration means for scheduling said high rate episode for a duration of at least about 10–20 minutes.

3. The system as described in claim 2, said high rate means further comprising de-activate means for de-activating operation of said high rate means, whereby a said episode lasts for the scheduled duration unless de-activated sooner.

4. The system as described in claim 1, wherein said duration means has means for scheduling said high rate episode for a duration of at least 20 minutes.

5. The system as described in claim 1, comprising at least one sensor for sensing a parameter reflective of the patient's heart response to a said high rate episode, and wherein said high rate means comprises de-activate means for deactivating said episode as a function of said sensed parameter.

6. The system as described in claim 5, comprising a plurality of sensors for sensing respective parameters reflective of the patient's heart response, and wherein said de-activate means comprises sensor algorithm means for determining from said sensed parameters whether said episode is to be de-activated.

7. The system as described in claim 1, comprising at least one sensor for sensing a parameter reflective of the patient's heart response to a said high rate episode, and wherein said algorithm means comprises adjust means for adjusting the rate during said episode as a function of said at least one sensed parameter.

8. The system as described in claim 7, wherein said adjust means lowers the rate to a value below said high rate range in response to said at least one sensed parameter meeting predetermined conditions.

9. The system as described in claim 1, wherein said algorithm increases rate gradually to a rate within said range at the start of a said episode, and decreases rate gradually to a rate below said range at the end of a said episode.

10. The system as described in claim 1, wherein said high rate means further comprises automatic activate means for automatically activating an episode at least once a day.

11. The system as described in claim 10, wherein said activate means comprises programmable means for activating a plurality of said episodes in a day.

12. The system as described in claim 10, wherein said activate means comprises a clock, and timing means to activate a said episode as a function of the patient's circadian rhythm.

13. The system as described in claim 1, comprising patient-activated means to activate and de-activate said high rate means.

14. The system as described in claim 1, comprising memory for storing data, sensor means for obtaining data indicative of the patient's cardiac responsiveness to rate changes, and means for selectively storing said data in said memory.

15. The system as described in claim 14, wherein said algorithm means comprises at least one stored algorithm for controlling rate variation, and comprising algorithm adjust means for adjusting said at least one algorithm as a function of said indicative data.

16. The system as described in claim 14, wherein said pacemaker is adapted to be implanted in said patient, and comprising a second device adapted to be implanted within said patient, said pacemaker having means for generating a control signal as a function of said stored data, and transmit means for transmitting said control signal to said second implanted device.

17. The system as described in claim 1, comprising program receive means for receiving programmed data, and programming means for programming said algorithm means in accordance with said programmed data.

18. The system as described in claim 1, comprising a plurality of sensors for obtaining data representative of patient cardiac responsiveness to high rate pacing, and means for adjusting a said episode in response to said data, and wherein said plurality of sensors includes sensors from a group which includes sensors for obtaining indications of ventricular pressure and ventricular volume.

19. The system as described in claim 1, wherein said high rate means comprises means enabled by said patient for initiating a said high rate episode following a start duration, and said algorithm means comprises an exercise rate algorithm which is designed to aid the patient to exercise, whereby the patient may initiate a high rate episode in anticipation of exercise.

20. The system as described in claim 19, wherein said algorithm comprises a start-up algorithm for increasing rate during said start duration in a manner to prepare said patient to undertake exercise during operation of said exercise algorithm.

21. The system as described in claim 19, comprising sensor means for obtaining a measure of patient activity during a said high rate episode, and wherein said high rate means comprises means for adjusting pace pulse rate during a said episode in response to said activity measure.

22. The system as described in claim 1, wherein said high rate means comprises means for obtaining a measure of patient exercise, and automatic means for initiating a said high rate episode as a function of said patient exercise measure.

23. The system as described in claim 22, further comprising an external device having a receiver and a display, and wherein said pacemaker has transmit means for transmitting data representative of patient performance to said external device for display to the patient.

24. A pacing system for providing pacing therapy to a patient, the system having a pace pulse generator and delivery means for delivering pace pulses to a patient's heart, and comprising control means for controlling the rate of generation and delivery of said pace pulses, said control means comprising at least one algorithm for determining an episode of high rate pacing, said algorithm providing for increasing pacing rate to at least a predetermined high value for a duration calculated to exercise said patient's cardiac muscle.

25. The pacing system as described in claim 24, comprising automatic means for automatically initiating said episode as a function of the patient's circadian rhythm.

26. The pacing system as described in claim 24, comprising patient-initiated means for initiating a said episode of high rate pacing.

27. The pacing system as described in claim 24, comprising automatic means for automatically initiating a said episode as a function of time.

28. The pacing system as described in claim 24, comprising sensor means for obtaining data reflective of patient exercise history, and means for initiating a said episode as a function of said exercise history data.

29. A pacing system for providing pacing therapy to a patient, the system having a pace pulse generator and delivery means for delivering pace pulses to a patient's heart, and comprising control means for controlling the rate of generation and delivery of said pace pulses, said control means comprising at least one algorithm for determining an episode of high rate pacing, said algorithm providing for increasing pacing rate to at least a predetermined high value for a duration calculated to exercise said patient's cardiac muscle and to aid said patient in exercising during at least a portion of said duration.

30. A method of high rate pacing therapy, comprising determining a high rate pacing duration suitable for exercising a patient's heart, and pacing said patient's heart at a rate in the range of 90–160 bpm for said determined duration.

31. The method as described in claim 30, comprising pacing at a variable rate within said range.

32. The method as described in claim 30, comprising pacing at a substantially constant rate for at least a portion of said duration.

33. The method as described in claim 30, further comprising sensing cardiac activity of said patient, and controlling said pacing as a function of said sensed activity.

34. The method as described in claim 33, comprising indicating to said patient when he or she can undertake exercise.

* * * * *